United States Patent [19]
Marangos et al.

[11] Patent Number: 5,910,127
[45] Date of Patent: Jun. 8, 1999

[54] ON-SITE EMERGENCY TREATMENT OF INJURED OR UNCONSCIOUS PATIENTS, USING FRUCTOSE-1,6-DIPHOSPHATE (FDP)

[75] Inventors: Paul J. Marangos, Encinitas; Anthony W. Fox, Rancho LaCosta; Brian W. Sullivan, Escondido, all of Calif.

[73] Assignee: Cypros Pharmaceutical Corp., Carlsbad, Calif.

[21] Appl. No.: 09/002,578

[22] Filed: Jan. 4, 1998

Related U.S. Application Data

[63] Continuation-in-part of application No. 08/646,600, May 8, 1996.
[51] Int. Cl.$^6$ .................................................. A61M 31/00
[52] U.S. Cl. ............................................................ 604/49
[58] Field of Search ........................... 604/49, 53, 65–67, 604/118, 246; 128/DIG. 12, DIG. 13

*Primary Examiner*—John D. Yasko
*Assistant Examiner*—Manuel Mandez
*Attorney, Agent, or Firm*—Patrick D. Kelly

[57] ABSTRACT

A method and device are disclosed which enable on-site pre-diagnostic emergency treatment of people suffering from life-threatening injuries (such as victims of auto accidents, shootings, stabbings, and near-drownings), or from a collapse or loss of consciousness that might be due to a heart attack, stroke, cardiac arrest, internal hemorrhage, or various other causes that cannot be diagnosed until after a physician or ambulance has arrived on the scene. This on-site pre-diagnostic emergency treatment involves intravenous injection of fructose-1,6-diphosphate (FDP, a naturally-occurring chemical which functions as an intermediate in glycolysis) into the patient. Such injections can be administered by police, firemen, military personnel, lifeguards, nursing home attendants, ambulance attendants, or anyone else who has been trained to administer intravenous injections. The FDP should be injected into the patient as soon as possible, without delaying until the patient can be diagnosed and treated by a doctor. When administered immediately, intravenously injected FDP can reduce ischemic or hypoxic damage to the internal organs, without having any adverse effects or posing any significant risks for patients who may not need it. Injection kits which include vials containing partially lyophilized FDP (which does not require refrigeration), sterile water for reconstitution of the freeze-dried FDP, and a syringe with hypodermic needles are also disclosed, in a hard-shell case that can withstand rough handling, as might occur in a police car or firetruck.

15 Claims, 6 Drawing Sheets

ON-SITE EMERGENCY TREATMENT OF INJURED OR UNCONSCIOUS PATIENTS, USING FRUCTOSE-1,6-DIPHOSPHATE (FDP)

RELATED APPLICATION

This application is a continuation-in-part of prior U.S. application Ser. No. 08/646,600, filed on May 8, 1996.

BACKGROUND OF THE INVENTION

This invention relates to a method of on-site emergency medical treatment for injured or unconscious patients. Using this invention, such treatment can be carried out by anyone trained to administer an intravenous injection (such as police, firemen, military personnel, lifeguards at swimming pools, nursing home attendants, etc.), without waiting for an ambulance to arrive, and without waiting for a medical diagnosis by a physician.

Under the prior art, no effective emergency medical treatment can be performed on injured or unconscious patients who still have a heartbeat (such as victims of accidents or violent crimes, or people who have suddenly lost consciousness without an obvious reason). Instead of effective medical treatment, people at the scene can only offer palliative care, such as laying a patient down and elevating his legs and feet above his head. Such palliative "first aid" does not rise to the level of genuinely effective medical treatment, as offered by this invention.

The difficulties and risks of treating shock victims (i.e., people who suffer a major loss of blood pressure after an injury) illustrate why it previously has been impossible to develop effective pre-diagnostic medical treatments for such victims. There are three different types of shock, and each type has its own set of causes, its own subtly different symptoms, and its own internal mechanisms that increase the severity of internal damage to the victim. These three different types of shock have been labelled:

1. hypovolemic shock, which normally occurs due to loss of blood from the vascular system;
2. cardiogenic shock, in which a heart attack, fibrillation, cardiac arrest, or other such crisis prevents the heart from beating properly;
3. hyperdynamic shock, in which the heart begins pumping too much blood, rather than too little. This can be caused by, for example, a septic infection in which bacteria release endotoxins that attack blood vessel walls.

These three different types of shock are described in more detail in Mouchawar et al, "A Pathophysiological Approach to the Patient in Shock," *Int. Anesthesiol. Clin.* 31:1–20 (1993). This is a review article which summarizes the various symptoms and uncertainties that doctors must deal with, when trying to figure out how to treat a patient who is in shock.

The crucial point of this analysis is this: proper drug treatment for one type of shock is very different from proper drug treatment for the other types of shock. As one example, vasodilating drugs (which dilate blood vessels) are widely used to treat cardiogenic shock (such as in heart attack victims), because they help reduce the stress on a struggling heart. However, the same vasodilator drugs that are very useful in that type of shock could be potentially deadly, if injected into someone suffering from either of the other two types of shock.

As a second example, inotropic drugs (which increase the pumping strength of the heart; dobutamine is an example) are often used for treating cardiogenic shock; however, it would be potentially lethal if used to treat hypovolemic or hyperdynamic shock.

It is essential to recognize that because of the differences between the three different types of shock, a previously known drug treatments which can help a patient suffering from one type of shock might harm or even kill a patient suffering from a different type of shock. Accordingly, since shock arises so often whenever a life-threatening injury occurs, it usually is deemed safest to do nothing except stand by and wait, until an ambulance arrives to carry the patient away.

The inability of bystanders (and even people trained in responding to emergencies, such as police, firemen, nursing home attendants, etc.) to provide any genuinely useful medical treatment is a tragic gap in modern medicine. Because of various cellular and physiological processes, the extent of damage to internal organs (especially the heart, brain, and kidneys) accelerates and grows rapidly worse, as the minutes pass by after a life-threatening injury or collapse. Rapid on-site emergency medical treatment of such victims, if available during the critical minutes immediately after a severe injury or collapse, could offer extraordinarily useful and humanitarian benefits in preventing death, and in minimizing permanent and potentially crippling damage to the heart, brain, and other organs.

Doctors and researchers have known this for many years, and yet, prior to this invention, there have been no significant breakthroughs of any sort, in terms of developing ways to provide on-site emergency drug treatments for critically injured accident or crime victims, or for people who suddenly collapse and lose consciousness for no apparent reason. As noted above, the only things that are actually done today, for critically injured or ill patients who still have a heartbeat, are limited to minor forms of palliative care, such as lying them down, keeping them warm, and elevating their legs above their heads.

Accordingly, one object of this invention is to disclose a method of emergency drug treatment, using fructose-1,6-diphosphate (FDP) in a form that can be injected into an injured or unconscious person immediately, at the scene of a life-threatening injury or collapse, by anyone who can administer an intravenous injection, without waiting for a doctor or ambulance to arrive.

Another object of this invention is to disclose an effective and beneficial drug treatment, using injectable FDP in a sterile and stable form that can be stored for long periods of time without requiring refrigeration, which can be injected safely into any severely ill, unconscious, or injured patient who needs immediate help, without jeopardizing the patient's status or recovery due to unknown or unforeseen medical factors, and without delaying treatment while waiting for a medical diagnosis.

A third object of this invention is to disclose that chemically stable and sterile partially-lyophilized (freeze-dried) FDP preparations inside sealed vials can be packaged in injection kits, which can be stored for months without refrigeration, in hard-shell kits that can be stored safely in locations such as police cars and firetrucks. If a medical crisis arises, the lyophilized FDP can be mixed with sterile water or saline solution (also contained in the kit, along with an injection syringe) to form an injectable liquid, which can be intravenously injected or infused immediately into the crisis victim. Such injection kits allow rapid and genuinely useful medical intervention, without requiring a medical diagnosis of the patient, and without waiting for an ambulance or doctor to reach the site of a crisis.

These and other objects of the invention will become more apparent through the following summary, drawings, and description of the preferred embodiments.

SUMMARY OF THE INVENTION

A method is disclosed for on-site pre-diagnostic emergency treatment of people suffering from life-threatening injuries (such as victims of auto accidents, shootings, stabbings, and near-drownings), or from a collapse or loss of consciousness that might be due to a heart attack, stroke, cardiac arrest, internal hemorrhage, or various other causes that cannot be diagnosed until after a physician or ambulance has arrived on the scene. This on-site pre-diagnostic emergency treatment involves intravenous injection of fructose-1,6-diphosphate (FDP, a naturally-occurring chemical which functions as an intermediate in glycolysis) into the patient. Such injections can be administered by police, firemen, military personnel, lifeguards, nursing home attendants, ambulance attendants, or anyone else who has been trained to administer intravenous injections. The FDP should be injected into the patient as soon as possible, without delaying until the patient can be diagnosed and treated by a doctor. When administered immediately, intravenously injected FDP can reduce ischemic or hypoxic damage to the internal organs, without having any adverse effects or posing any significant risks for patients who may not need it.

DESCRIPTION OF THE PREFERRED EMBODIMENTS

This invention discloses a method for on-site pre-diagnostic emergency treatment of a patient suffering from a life-threatening injury (such as due to an automobile accident, shooting, or stabbing), a near-asphyxiation (due to drowning, suffocation, carbon monoxide poisoning, etc.), or a collapse or loss of consciousness or coherence that might be due to a heart attack, stroke, cardiac arrest, internal hemorrhage, or various other causes that cannot be fully diagnosed until after a physician or ambulance has arrived on the scene. Such conditions are referred to herein, collectively, as "life-threatening medical crises". All of these life-threatening crises involve ischemia (inadequate blood supply to the internal organs, as can be caused by a loss of blood, internal hemorrhage, heart attack, etc.) and/or hypoxia (inadequate oxygen supply, which occurs as a direct result of ischemia, and also as a result of certain other crises such as asphyxiation or carbon monoxide poisoning).

The treatment involves intravenously injecting or infusing a liquid solution containing fructose-1,6-diphosphate (FDP, a naturally-occurring chemical which functions as an intermediate in glycolysis) into a patient or accident victim as soon as possible after the onset of a crisis such as an injury or a sudden and unexplained loss of consciousness or coherence. This injection of FDP should not be delayed until an ambulance or doctor arrives; instead, for maximal benefit, it should be administered as soon as possible, preferably at the site of the accident or other emergency, by anyone who has been trained to administer an intravenous injection (such as police, firemen, military personnel, nursing home attendants, lifeguards, and relatives of people who suffer from chronic diseases such as heart disease).

FDP, in the partially-lyophilized form disclosed herein, can also be carried in ambulances, and can be administered by ambulance attendants as soon as they arrive at the scene of an injury or collapse, without waiting for the patient to be transported to a hospital.

When FDP is administered as quickly as possible to a patient suffering a life-threatening injury or other crisis, it can substantially reduce cell death and tissue damage in internal organs that have become or are in danger of becoming ischemic or hypoxic. However, if FDP is administered to someone who does not need it and will not benefit from it, it will not create any known significant adverse effects, or pose any known significant risks.

This combination of traits—protective benefits in people who need it, and very low risk in people who don't need it—render FDP well-suited for on-site pre-diagnostic use in medical emergencies, using injections that can be administered immediately, before an ambulance arrives, and long before a patient can be transported to a hospital for treatment by fully qualified physicians with extensive diagnostic equipment. As is well known to physicians, the speed with which proper care is initiated often makes a critical difference in survival, in the extent of internal damage (including permanent and crippling damage) suffered by victims of life-threatening injuries or illnesses, and in the personal, family, and social costs and burdens that result from major medical emergencies.

Partially-Lyophilized FDP

It has been known for nearly 20 years that FDP might be able to help reduce organ damage after ischemic crises, and there is a long list of articles and patents which suggest that type of medical use. Examples of such articles, which stretch back to at least 1980, include Markov et al 1980, 1986, and 1987, Brunswick et al 1982, Granot et al 1985, Farias et al 1986, Grandi et al 1988, Zhang et al 1988, Cacioli et al 1988, and Lazzarino et al 1989 and 1992. Relevant U.S. patents include U.S. Pat. Nos.4,546,095 (Markov 1985), 4,703,040 (Markov 1987), and 4,757,052 (Markov 1988).

Despite all of these prior suggestions, it previously has not been feasible or practical to use FDP as an on-site treatment for medical emergencies, because FDP is chemically unstable, and it spontaneously degrades to form useless by-products. Accordingly, storage of aqueous solutions for more than a week or two would require refrigeration, which is not feasible for most locations, such as police cars, firetrucks, ambulances, etc.

Although several companies and researchers have tried to develop lyophilized preparations of FDP, none of those prior efforts ever succeeded in actually producing any FDP that could be sold and used to treat humans, in nations that have high and strict quality controls on drug purity. The only known preparation of lyophilized FDP which is commercially available anywhere in the world is by an Italian company called Biochemica Foscama. However, this preparation apparently does not have sufficient purity to qualify for sale and use in the United States, and the company that makes it has never even attempted to apply for FDA approval to sell it in the U.S.

Other dried FDP preparations have been made in Japan and China, as disclosed in U.S. Pat. No. 5,094,947 (issued in 1992 to Nakajima et al, based on a prior Japanese application) and Chinese patents 1,089,615; 1,089,616; and 1,089,654, invented by Ou-Yang et al). However, those apparently have not been developed any further, and apparently, no effort has been made to commercialize them or obtain approval to sell them for human use in the U.S.

Recently, the Applicant/assignee company (Cypros Pharmaceutical Corporation) has created a new method for lyophilizing FDP in a sterile and stable form that is completely suited for obtaining complete approval from the FDA for public use and sale. Unlike any other prior efforts by any other company or researcher, this newly developed method uses sterilizing and manufacturing techniques that are carefully selected and designed to create a completely sterile and stable formulation, in a sealed two-chamber vial that contains both the FDP and a sterile aqueous solution. The vial can maintain complete sterility of both the FDP and the water until the FDP is needed, when a medical crisis arises. At that time, the FDP and the water can be mixed wile still inside the sealed vial, then the solution can be withdrawn from the vial using a hypodermic needle which is pushed through a sealing plug on the vial.

The sterilizing and lyophilizing processes are described in more detail in Example 1, and in a separate co-pending U.S. patent application, Ser. No. 08/705,773, owned by the same Applicant/assignee company herein. That patent application has been allowed, and it will issue in 1998 as a U.S. patent. The contents of that application (and the patent arising from it) are incorporated herein by reference.

Figure 1:
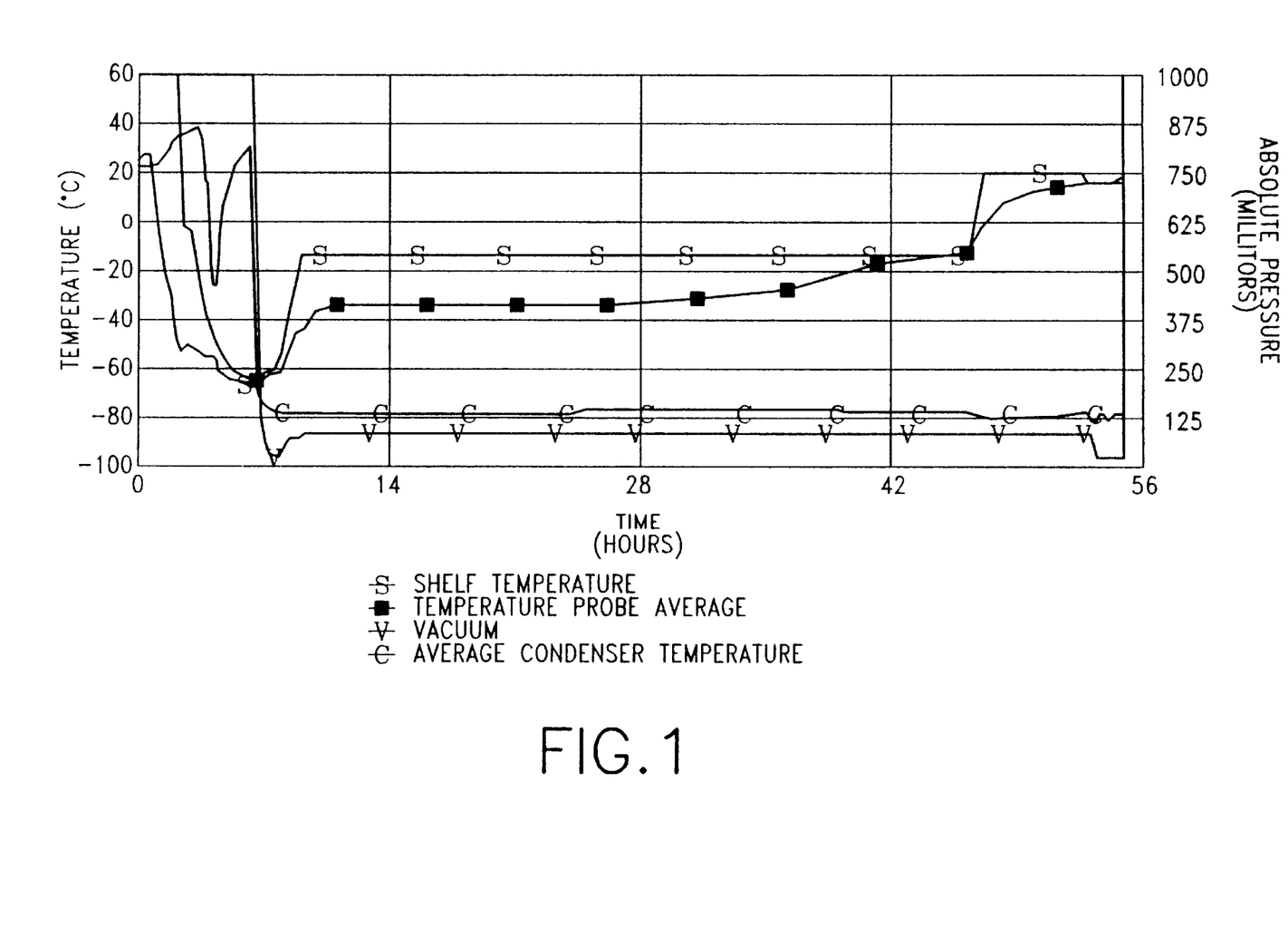
FIG. 1 is a chart of temperatures and pressures used to create partially-lyophilized FDP having residual water content of about 12 to 14% by weight. This high level of residual water (in most lyophilized drugs, water levels must be reduced to only about 2% or less) was found to provide very good chemical stability for FDP for long periods of time (i.e., months and possibly years).

Briefly, a supply of FDP in non-sterile bulk powdered form (available from several suppliers; purchased as a tri-sodium octahydrate salt from Boehringer Mannheim, in Germany) was dissolved in sterile water. Preferred concentrations which gave the best lyophilization performance were in the range of about 30 to 40% FDP, by weight. The dissolved solution was passed through a filter with a pore size of 0.2 microns, which is small enough to remove any bacteria or viral particles, thereby serving as a sterilization step. Filtered sterile solutions were filled into 100 mL molded glass vials, usually after being mixed with a secondary vaporizing agent such as tertiary butyl alcohol to reduce lyophilizing time and improve the quality and consistency of the final product. The loaded vials were then placed in a lyophilizing chamber, and subjected to a suitable combination of freezing temperatures and vacuums (one such profile, showing temperature and vacuum as a function of time, is shown in FIG. 1), usually for a period of about 2 to about 5 days, depending on various parameters. Lyophilization was continued until the residual water content was reduced to a range of about 10% to about 25%; the preferred range which gave the most consistent high-quality results was about 12% to about 16% residual water, by weight. The lyophilization was terminated, and the vials were sealed while still inside the chamber, to prevent any risk of losing sterility.

Figure 2:
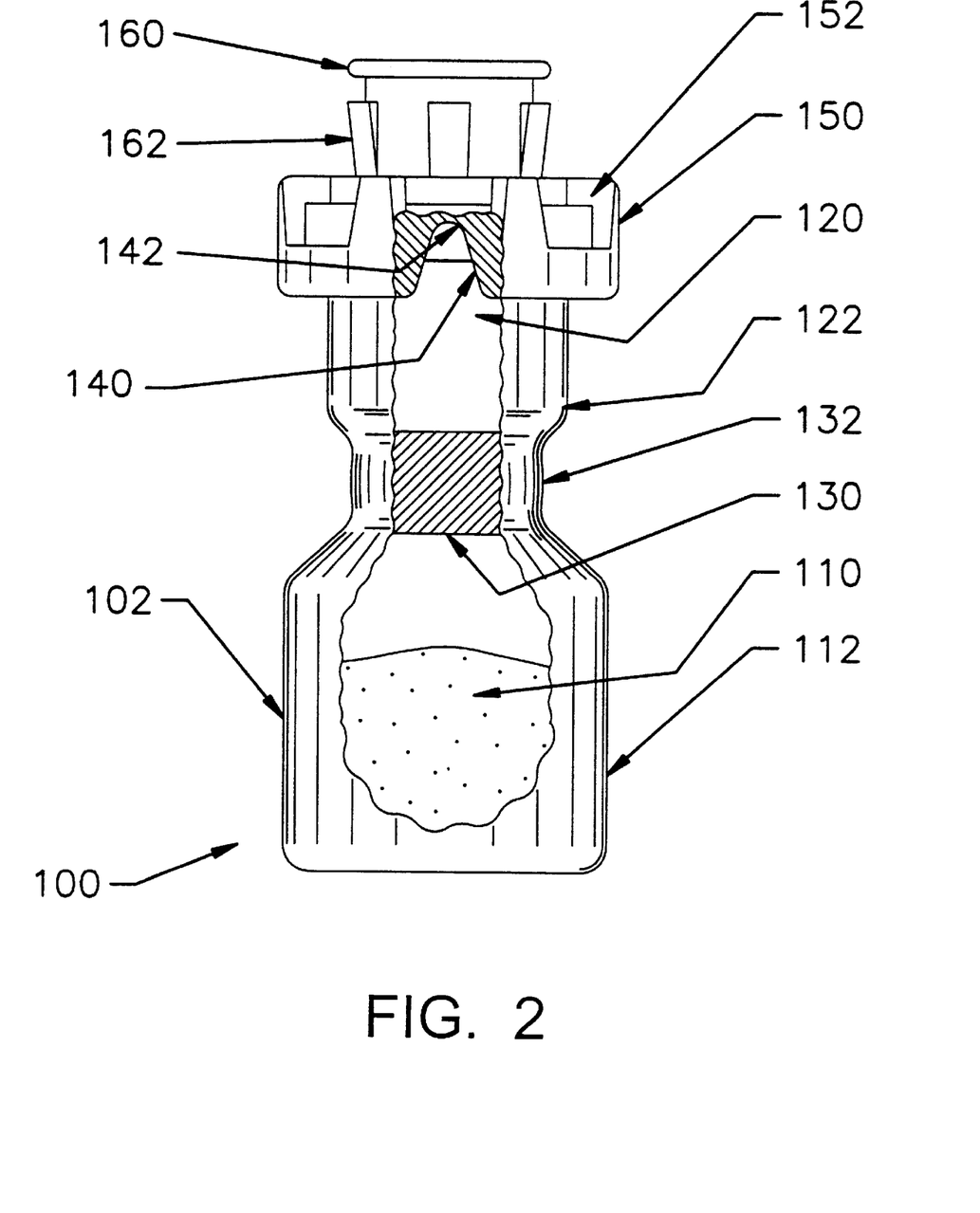
FIG. 2 is a cross-sectional view of a two-chamber vial containing sterile water or saline solution in the top chamber, and partially-lyophilized FDP in the bottom chamber, with a rubber "septum" separating the two components. When the top of the vial is forced down, the septum is pushed down into the bottom chamber, allowing the water and FDP to be mixed together to form an injectable solution.

FIG. 2 is a cross-sectional view of a two-chamber vial assembly 100, which can be used to store both FDP and sterile water (or other aqueous solution, such as a physiological saline solution) under completely sterile conditions. This type of two-chamber vial is known in the art, and is shown in various U.S. patents, including U.S. Pat. No. 4,781,354 (Potts 1981). This vial assembly comprises an outer wall 102 which is roughly cylindrical with a flat bottom, and which defines and enclosed a lower chamber 112 (which must be filled first, during the manufacturing process) and an upper chamber 122, separated from each other by a narrower constriction band 132.

This two-chamber vial structure is conventional and well-known, and the point of novelty of the vial shown in FIG. 2 is that it contains a partially lyophilized FDP powder or cake 110, as disclosed herein, in lower chamber 112. The vial also contains sterile water 120 (preferably in a solution intended for injection that also contains other conventional ingredients such as dextrose, Ringer's lactate, etc.), in upper chamber 122.

The two chambers 112 and 122 are separated from each other by a water-tight partition or "septum" 130, which is a non-permeable disk made of an inert flexible material such as butyl or silicone rubber, which has been force-fitted into the constriction band 132, which holds septum 130 in place until the FDP is needed.

A second non-rigid plug 140, usually made of butyl rubber, is mounted in the neck of the vial, and is secured to the vial by means of a metallic cap 150. This soft, flexible plug 140 allows a sharp tip of a hypodermic or tubing needle to be inserted into upper chamber 122, through a relatively thin upper wall portion 142 of the plug 140. This allows removal of a reconstituted liquid from the vial, so that the liquid can be loaded into a hypodermic syringe or infusion bag, for injection into a patient. The soft plug 140 interacts wit a hypodermic needle 212 (as discussed below) to provide a means for transferring a reconstituted injectable formulation (i.e., the FDP 110, after it has been mixed with the sterile water 120) into the barrel of a syringe, without exposing the formulation to outside air and an attendant risk of contamination.

The metallic cap 150 interacts with plunger 160, allowing the plunger to be forced down, through an orifice which occupies the center of the cap 150. Outward-extending locking ears 162 in the sides of plunger 160 interact with accommodating slots 152 in the metallic cap, to lock the plunger in position once it has been pushed down into the cap.

When an emergency arises and the FDP is needed for injection into a patient, plunger 160 is depressed. This pushes septum 130 out of position in the constriction band 132, aided by two factors: (a) the inert gas (usually nitrogen or argon) that fills the top of chamber 112 is compressible and allows downward motion of the septum 130 under pressure; and (2) the aqueous liquid which fills the upper chamber is non-compressible, and causes the full force placed on plunger 160 to be pressed against the movable septum 130.

As soon as the septum 130 falls into the lower chamber 112, the dry FDP 110 comes into contact with the aqueous solution 120, and the two are mixed together thoroughly, by shaking the vial. The septum can bounce around inside the lower chamber 112 during this shaking process, and acts as a mechanical agitator to promote full mixing, and to help rapidly break apart the cake, if the dry FDP 110 was in a solidified cake rather than a powder.

The term "vial" is used broadly herein, to refer to any drug-packaging device that is designed and suitable for sealed and sterile storage, shipping, and handling of small (e.g., single-dosage) quantities of drugs. The two-chamber vial shown in FIG. 2 is only one example of the various types of two-chamber vials that are known in the art. Single-chamber vials are also well known; for example, a single-chamber vial designed for use with intravenous infusion bags (which are carried by any ambulance, and which can enable injection of much larger quantities of liquid drugs than conventional syringes) is illustrated in U.S. Pat. No. 4,871,354.

Figure 3:
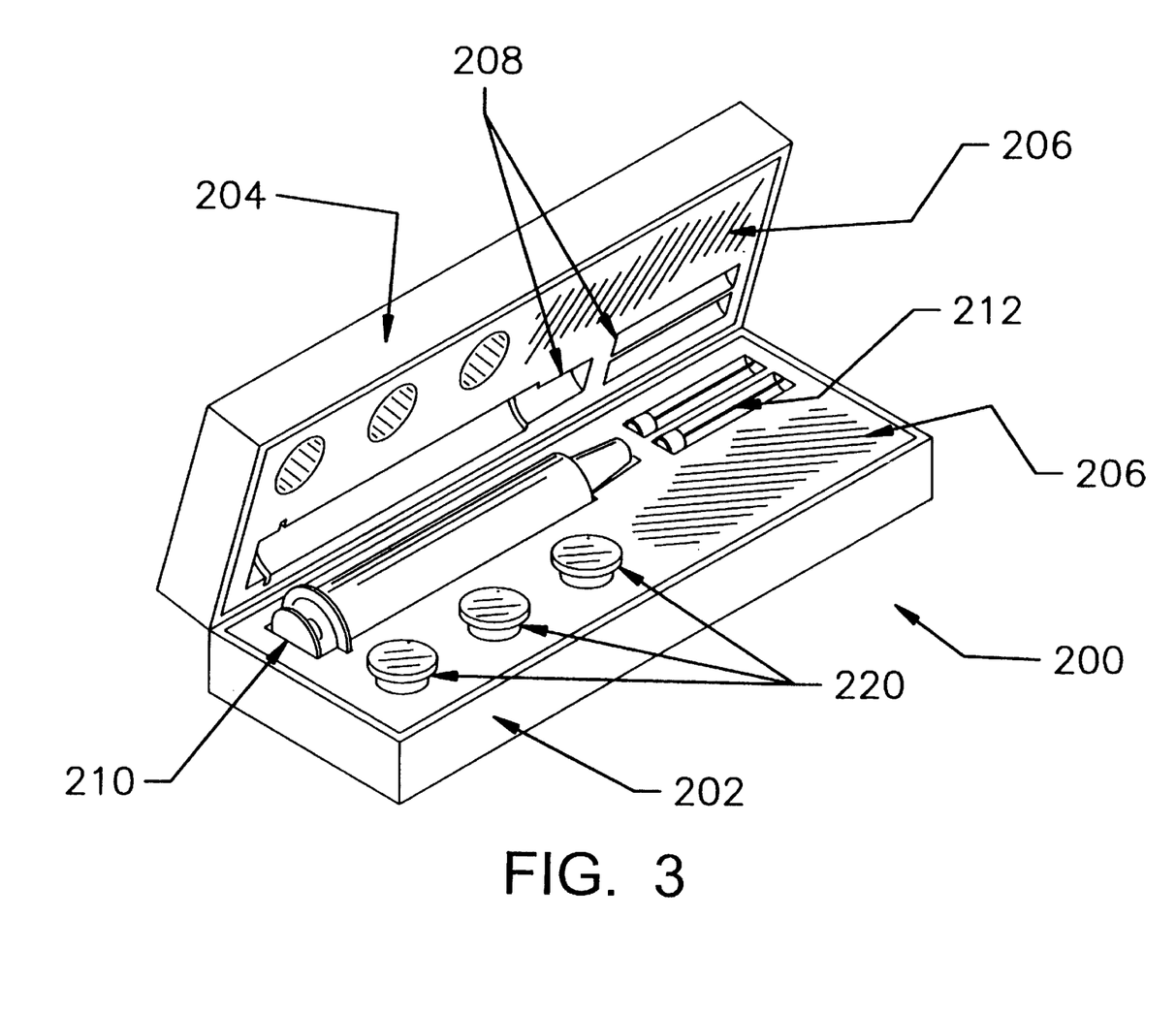
FIG. 3 depicts an injection kit for emergency use at the site of a medical crisis, with a durable hard-shell case that holds a syringe, hypodermic needles, and several vials containing FDP and water as shown in FIG. 2. Such FDP injection kits can be kept in police cars, firetrucks, nursing homes, the homes of people with certain chronic diseases, and other such locations, and the lyophilized FDP will remain chemically stable and pure for months without requiring refrigeration.

One or more vials 100 (either two-chambered vials as shown, for use in police cars, firetrucks, etc., or single-chamber vials for use with infusion bags in ambulances, nursing homes, etc.) can be included in an emergency injection kit 200, shown in FIG. 3. This kit 200 is enclosed in a durable hard-shell case having a bottom portion 202 and a hinge-attached top portion 204, made of a molded material such as a hard plastic. The external shell can also enclose padding material 206, made of, for example, a lightweight, highly porous foam rubber which has been machined to provide shaped cutaway pockets 208 which will securely hold syringe 210, hypodermic needles 212 (preferably, at least two needles should be provided, in case one gets damaged), and vials 220 containing lyophilized FDP (as many vials as desired can be provided, each vial containing a standard quantity of FDP, such as 5 grams). This will allow the case and padding material to protect the fragile contents without being damaged, even if subjected to fairly rough treatment, as might occur, for example, in the trunk of a police car. The syringe and needle can be carried in separated cutaway holders inside the hard-shell case. The syringe can be sealed inside a sterile plastic wrapper (not shown), and each needle can be carried inside a small rigid plastic shell (not shown), to protect it and prevent it from jabbing anything.

The inclusion of lyophilized FDP in this type of emergency injection kit 200 as shown in FIG. 3 can allow immediate on-site treatment of a patient or victim of a severe medical crisis (such as a heart attack, shooting or stabbing, or auto accident) by anyone who can administer an intravenous injection. This may include, for example, ambulance attendants, police, firemen, nurses, nursing home attendants, emergency room attendants, lifeguards, and relatives of people who suffer from various diseases, such as heart disease or sickle cell anemia.

Accordingly, the emergency injection kit 200 does not require refrigeration, and it is designed to withstand the type of rough treatment that might occur if carried in ambulances, police cars, firetrucks, etc., or if stored in first aid cabinets, boxes, or closets, at locations such as nursing homes, lifeguard stations, and in the homes of people suffering from various diseases, such as heart disease or sickle cell anemia.

As noted below, all references herein to FDP are deemed to include salts of FDP, such as sodium salts. However, references herein to FDP do not include other isomers such as fructose-2,6-diphosphate, which are not useful for the purposes disclosed herein.

The dried, sterile, stable FDP preparations disclosed herein, having more than 10% residual water, are referred to interchangeably herein as either "partially lyophilized" or "lyophilized". They are lyophilized, since they have indeed been subjected to a lyophilization process. However, they must be recognized as being only partially lyophilized, when measured by conventional lyophilization standards for pharmaceutical products. Most lyophilized drugs require that the residual water content be reduced to about 2% or less, in order to ensure chemical stability of the resulting drug. Accordingly, the discovery that the best results and highest levels of stability could be obtained at ranges of about 12% to about 16% water, was completely unexpected, especially since the primary type of instability of FDP involves hydrolyzing of either phosphate group from the di-phosphate compound, to create a mono-phosphate compound. Such mono-phosphates are completely useless in glycolysis, and have no value in the subject invention; they are regarded as impurities.

It should also be noted that, when measuring the purity of lyophilized FDP, residual water and sodium are not regarded as impurities, since they are desirable constituents which help stabilize the FDP preparation.

Factors Which Have Taught Away from Public Use of FDP

There are a number of reasons why FDP has not previously received serious attention by any drug development companies that might be capable of actually manufacturing and selling it in commercial quantities. Those reasons include:

(1) FDP is a diphosphate with a strong negative charge, and it is generally assumed by doctors and researchers that its highly-charged nature will prevent it from entering cells in substantial quantities. Since energy metabolism and glycolysis occur inside cells, it is generally assumed that FDP will not reach the relevant sites in adequate quantities to do any substantial good.

(2) It is also believed and assumed that FDP does not penetrate a mammalian blood-brain barrier in significant quantities, and therefore will be of little or no utility in protecting the brain and central nervous system against CNS damage caused by ischemia or hypoxia.

(3) Directly contradicting the articles which suggest that FDP has some level of beneficial effects, a number of articles have reported that FDP had no beneficial effects in various other studies. Examples of these negative articles include Eddy et al 1981, Pasque et al 1984, Tortosa et al 1993, and Angelos et al 1993.

(4) The amount of energy generated during glycolysis (i.e., when a molecule of glucose containing 6 carbon atoms is split apart into 2 molecules of pyruvate, with 3 carbons each) is only a small fraction of the energy generated by the aerobic (Krebs Cycle) oxidation of pyruvic acid to form carbon dioxide and water. If not enough oxygen is present, then the breakdown of pyruvate follows a completely different pathway which generates lactic acid (which is basically a toxin, as described below) instead of carbon dioxide and water. This conversion of pyruvate into lactic acid releases a relatively small amount of useful energy in the form of ATP; however, the amount of energy produced by this oxygen-starved reaction is only a small fraction of what would be produced by complete oxidation of pyruvate to form carbon dioxide ad water.

Therefore, under conditions of ischemia or hypoxia, where an oxygen deficit prevents aerobic oxidation of pyruvate and instead leads to the creation of lactic acid, it is assumed that FDP infusion would be insufficient to supplement ATP levels to a degree that can significantly aid cell survival.

These biochemical factors set the stage for the crucial problem in administering FDP to patients suffering from ischemic or hypoxic crises. That problem is discussed in the following subsection.

Concerns over Excess Lactic Acid and the PFK Enzyme

In tissue suffering from ischemia or hypoxia, the addition of FDP to the system causes a substantial increase in the concentrations of lactic acid. For example, in research described in Lazzarino et al 1992, when radioactively-labelled FDP was added to perfused isolated hearts, about 90% of the exogenous FDP was converted into lactic acid. Only about 10% of the FDP was fully oxidized to form carbon dioxide and water.

This problem has been regarded as a major impediment, which apparently blocks the safe and effective use of FDP in victims of ischemia or hypoxia, because excess quantities of lactic acid (produced as the major product of exogenous FDP, under conditions of ischemia or hypoxia) poses a major risk of poisoning and inactivating a crucial enzyme called phosphofructokinase (PFK).

The PFK enzyme is essential for glycolysis; because of certain biochemical factors, PFK controls and limits the overall process of glycolysis. By way of illustration, pages 266–267 from Stryer 1981 state emphatically, first as a heading, and then in italics: "PHOSPHOFRUCTOKINASE IS THE KEY ENZYME IN THE CONTROL OF GLYCOLYSIS . . . Phosphofructokinase is the most important control element in glycolysis."

Accordingly, there is a substantial fear and presumption, among doctors and researchers, that injecting exogenous FDP into the blood of someone suffering from an ischemic or hypoxic crisis may shut down the entire process of glycolysis, by poisoning the crucial PFK enzyme. The general presumption among doctors and researchers has been that this high-level risk is not worth any low-level, short-term benefits that might be obtained when pyruvate molecules are converted into lactic acid using the low-yield, anaerobic pathway.

For these and other reasons, it appears that little if any effort has been directed by the pharmaceutical industry toward developing FDP as a useful drug. Under the laws enforced by the U.S. Food and Drug Administration, FDP cannot be sold in the United States for administration to human patients by physicians, and FDP simply is not administered to any patients, on any sort of routine basis.

However, it appears that those fears and presumptions about possible poisoning of the PFK enzyme by elevated lactate levels apparently do not pose a major risk, so long as the patient still has a heartbeat and has not suffered complete cardiac arrest. This is supported by three different sets of data: (i) data gathered recently in tests on patients who suffer from sickle cell anemia, who are compromised in their ability to properly handle oxygen transport via red blood cells; (ii) data gathered during coronary artery bypass surgery, on compromised patients who were suffering from chronic cardiac ischemia; and (iii) various items of data scattered throughout the scientific and medical literature on FDP.

Briefly, it appears that injections or infusions of FDP provide enough energy (in the form of ATP, which is generated by both (i) cleavage of the FDP into pyruvate, which creates 4 molecules of ATP, and (ii) subsequent metabolism of the pyruvate into varying proportions of lactic acid, carbon dioxide, and water, depending on the oxygen content of the cells) to temporarily boost the system, and get it going again well enough to handle any surplus of lactic acid.

Several factors should be borne in mind, concerning the fates and effects of lactic acid in partially-ischemic tissue that has received an exogenous supply of FDP from an injection. First, lactic acid readily permeates out of cells, and enters the circulating blood, where it is handled and eliminated very efficiently by the liver, via several different mechanisms. In particular, the conversion of pyruvate to lactic acid is a completely reversible reaction; if ATP is present to drive the reaction, then lactic acid is normally converted back into pyruvate, mainly but not exclusively in the liver, and the resulting pyruvate is then oxidized to carbon dioxide and water, releasing large amounts of energy.

If a patient is suffering a heart attack or stroke, or even a near-suffocation (enough to threaten severe damage to the brain, but not enough to seriously disrupt liver functioning), the liver will be relatively unaffected, and it will be able to convert excess lactic acid back into pyruvate. As noted above, the pyruvate can then be oxidized to carbon dioxide and water, if oxygen remains present in the liver. This will generate large quantities of energy-rich ATP, which can help restore proper homeostasis in the patient's body. This same process (i.e., conversion of lactate back into pyruvate, followed by oxidation of the pyruvate to release large quantities of energy) occurs not just in the liver, but in other organs and blood cells as well.

This type of highly beneficial process is evidenced by data gathered recently in tests on patients suffering from sickle cell anemia. In a sickle cell patient, red blood cells have defective hemoglobin genes, which causes them to undergo a shape-changing process under conditions of low oxygen supply. Under normal conditions, red blood cells are relatively pliable and can be deformed readily. This allows them to squeeze through capillary openings that are smaller than the cells; this deforming process promotes the release of oxygen by the cells, thereby increasing the amount of oxygen supplied to the surrounding tissue. However, during a sickling crisis, the pliable round cells take on a rigid, non-yielding, curved shape, like the blade of a sickle used to harvest grain, due to crystallization of the defective hemoglobin molecules. When this happens, the sickle-shaped red blood cells lose their flexibility and can no longer squeeze through narrow capillaries. These blood cells begin clogging up capillaries, blocking blood flow through the capillaries. This soon escalates into a full-scale crisis, as the affected tissue that is normally served by the blocked capillaries quickly becomes starved for oxygen, which further depletes any nearby red blood cells and causes them to become even more sickled and rigid.

In a set of clinical and laboratory tests carried out by the same Applicant/assignee company herein, FDP was intravenously injected into the blood of patients who were suffering from full-blown sickle cell crises. As described in a separate co-pending patent application, the FDP worked quite well, and helped the patients overcome their crises more rapidly and with substantially less pain than in control patients who received only the conventional non-FDP treatment for sickling crises.

The data gathered from these tests on blood from sickle cell patients display an unusual and unexpected effect on lactic acid levels, after the blood was treated using FDP. As described in Example 3, treatment of blood samples using FDP caused a reduction, rather than an increase, of lactate levels in the blood samples. This was true in blood samples taken from sickle cell patients, and in blood samples taken from healthy volunteers who do not have the disease.

These results, and the biochemical processes that underlie and explain these results, indicate that FDP, rather than causing severe increases in lactic acid which would jeopardize the PFK enzyme and the entire glycolytic pathway, instead can have substantially beneficial effects even under conditions of mild or localized hypoxia. Apparently, in at least some situations, FDP can even reduce the amount of lactic acid formed, rather than increasing it, by providing enough energy to (1) convert lactic acid back to pyruvate, and (2) help jump-start the oxidation of pyruvate into carbon dioxide and water, which can release large quantities of energy even in mildly hypoxic tissue.

Figure 4:
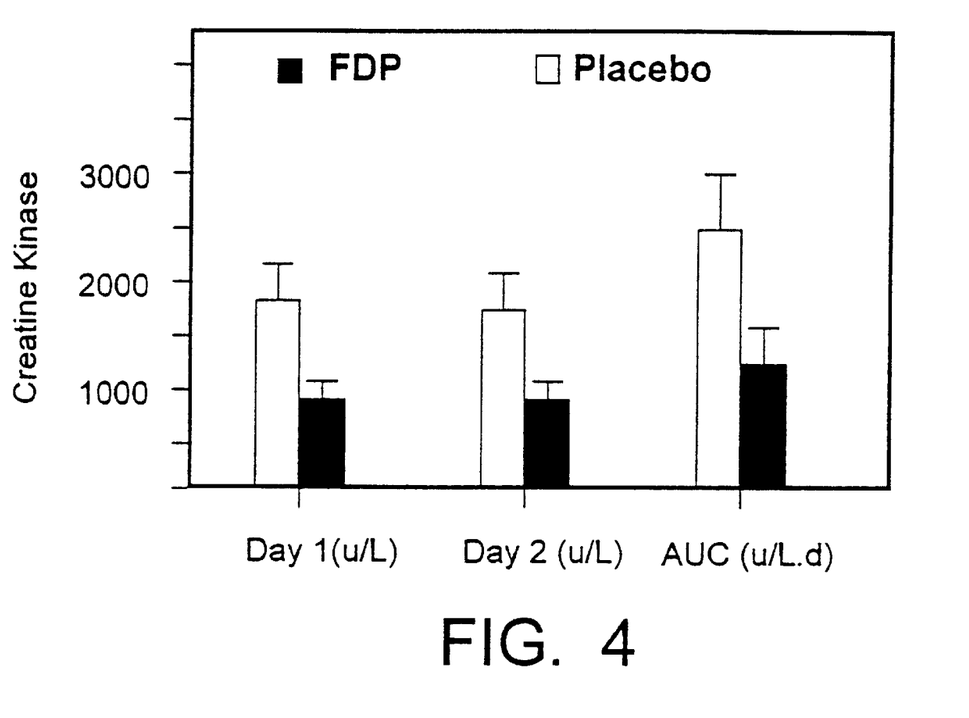
FIG. 4 is a graph showing creatine kinase (CK) levels in blood serum, measured in clinical trials involving cardiac surgery in which the heart was stopped and the patient was placed on cardiopulmonary bypass. Comparison of FDP-treated patients to untreated patients shows that FDP substantially reduced cell death in ischemic heart tissue.

An entirely separate set of tests, on patients undergoing surgery to provide coronary artery bypass grafts (CABG), also showed that FDP caused no ill effects, of any sort, on impaired patients who had been suffering from chronic cardiac ischemia which was bad enough to require surgery. The results of these tests, discussed in more detail in Example 4, indicated that, rather than causing any problems related to excess lactate production, the FDP treatment provided two major benefits:

(i) a substantial reduction in blood-borne levels of an enzyme called creatine kinase, after surgery, compared to untreated control patients. Creatine kinase (CK) is a very large enzyme that cannot leave cells by permeating through cell membranes; instead, it escapes form cells only after the cells die and their membranes rupture. Accordingly, CK levels in circulating blood offer a good indicator of the extent of cell damage and death, in patients who have suffered heart attacks or who have undergone cardiac surgery. As shown in FIG. 4, FDP treatment substantially reduces this biochemical indicator of cardiac cell damage, compared to untreated control populations.

Figure 5:
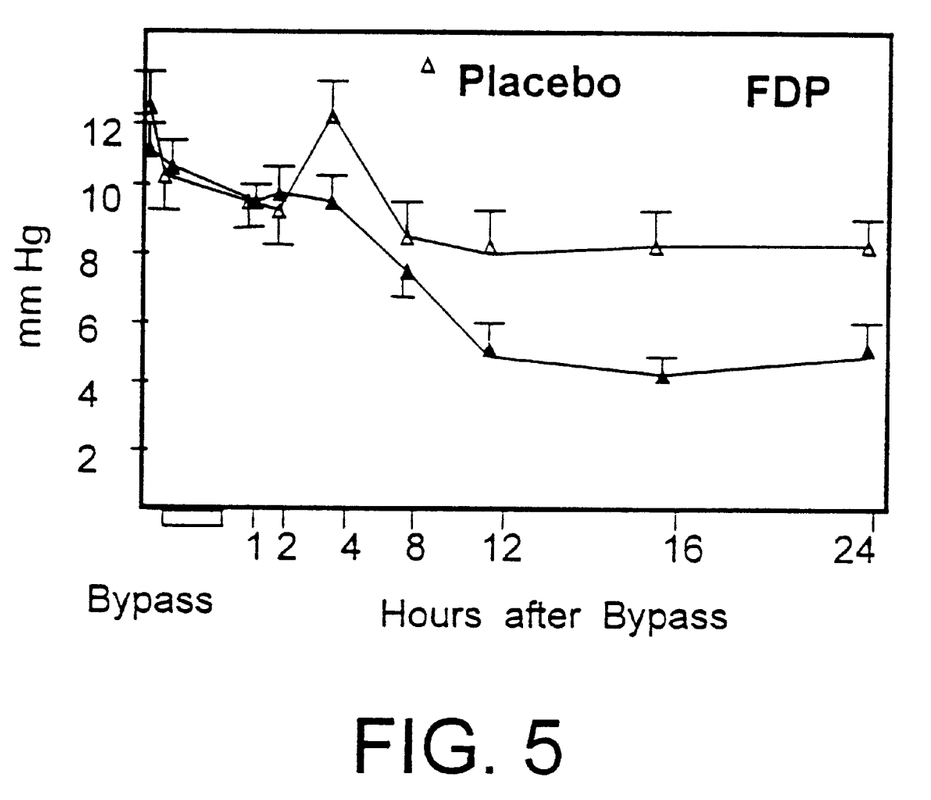
FIG. 5 is a graph comparing heart pumping capability, as measured by "pulmonary artery wedge pressure" (PAWP), in FDP-treated patients compared to control patients, in clinical trials where the heart was stopped and the patient was placed on cardiopulmonary bypass during surgery. These results show that FDP substantially reduced the damage to the hemodynamic performance of the hearts caused by ischemia during surgery.

(ii) a substantial reduction in unwanted abnormalities in an indicator of cardiac pumping performance, called "pulmonary artery wedge pressure"(PAWP). If PAWP values increase by large amounts after bypass, compared to PAWP values measured before bypass, the large increases indicate that the heart suffered high levels of stress and damage during the ischemic/hypoxic conditions that arose during bypass. As shown in FIG. 5, FDP treatment substantially reduced these elevations in PAWP values, compared to the substantially larger increases in PAWP values in control patients who did not receive FDP treatment.

Figure 6:
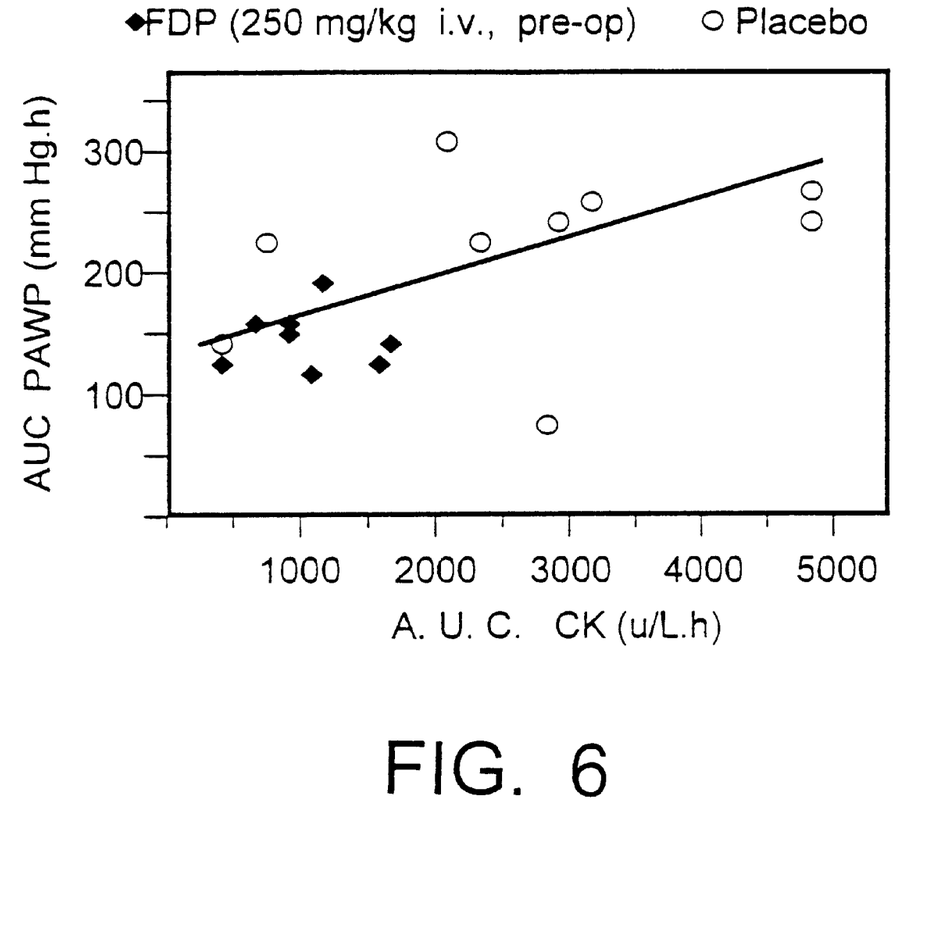
FIG. 6 is a graph which shows how the biochemical benefits of FDP (as measured by creatine kinase levels in the blood) correlate with the mechanical and hemodynamic benefits of FDP (as measured by reduced elevations in PAWP values). This correlation confirms that FDP provided both biochemical and hemodynamic benefits, and reduced the overall damage inflicted on the hearts due to ischemia and hypoxia during surgery.

In addition, as shown in FIG. 6, the CK reductions and PAWP value reductions caused by FDP treatment were correlated with each other. This correlation confirms that FDP treatment was indeed responsible for substantially better overall outcomes, in FDP-treated patients compared to control patients.

In addition, monitoring of blood acidity levels in the surgical patients indicated that FDP caused only a slight increase in blood acidity (presumably due to lactic acid), in patients who received the highest dosages of FDP, totalling 750 mg/kg over a span of about 7–8 hours. The increase in acidity was mild, and did not require any intervention (such as bicarbonate treatment). None of the patients who received lower dosages of FDP showed any significant alterations in blood acidity. This result is described in more detail in Example 4.

As noted above, the surgical data and the data from sickle cell anemia patients were all gathered from patients who were struggling with medical conditions that rendered them chronically ischemic and hypoxic. Accordingly, the beneficial and useful results from all tests completed to date on medically-compromised patients add to and support the overall conclusion that FDP can be used safely, with little or no risk or downside potential, even in medically-compromised patients who are suffering from various forms of ischemia and/or hypoxia.

Medical Conditions Which Warrant Immediate Injection of FDP

Various medical symptoms that warrant immediate intravenous injection of FDP by a trained caregiver, without waiting for a full diagnosis by a physician, are listed below. FDP is not recommended or required for minor events; instead, it should be used in situations which indicate a major medical emergency that appears to be severe enough to require an immediate trip to a hospital for full diagnosis and treatment. As noted above, these conditions are referred to collectively as "life-threatening medical crises". Such conditions include:

1. Substantial loss of blood. This may be due to an accidental injury (such as an auto accident, a fall, mangling by machinery or tools, etc.), an assault such as a shooting or stabbing, and other traumas or injuries which causes a patient or victim to lose a substantial quantity of blood in a visible, external manner.

2. Abnormalities in pulse which are sufficiently severe to indicate a potential heart attack, cardiac arrest, internal hemorrhage or hemorrhagic shock, or severe allergic reaction. Such abnormalities can include abnormally rapid heartbeat (tachycardia, which in extreme cases becomes fibrillation), abnormally slow heartbeat (bradycardia), arrhythmia (irregularities in the heartbeat), and severe faintness or weakness of the pulse.

3. Symptoms of heart ischemia which may indicate a potential impending heart attack, such as unexplained dizziness or light-headedness, or numbness in one of the limbs (especially in a shoulder or arm).

4. Electrical shock, if sufficiently severe to pose a serious risk of disrupting heart functioning.

5. Asphyxiation, such as a near-drowning, near-suffocation, or carbon monoxide poisoning.
6. Loss of consciousness, mental disorientation, unresponsiveness, or an inability to control normal motor functions (such as an inability to walk, stand up, or sit up straight), if such condition does not appear to be related to use of drugs or alcohol or to any other obvious explanation.
7. Other conditions that suggest the possibility of serious internal bleeding, such as sudden pallor accompanied by faintness or mental disorientation.
8. Severe and unexplained shortness of breath, as might be caused by a cardiopulmonary event such as a heart valve failure.

If a person loses consciousness, coherence, or motor control with no reason to suspect drug or alcohol abuse and no other clear explanation, it may be due to any of several types of internal crises, such as stroke, internal hemorrhage, severe allergic reaction to an insect sting or prescription drug, etc. In some cases where these symptoms indicate a medical emergency, injection of FDP may be able to offer extremely useful and beneficial help.

There is no consensus among physicians and medical researchers as to whether FDP may be able to help protect brain tissue following a stroke. Most physicians and researchers generally presume that FDP will not be able to permeate through a mammalian blood-brain barrier in quantities large enough to have any significant effect. However, a careful reading of the literature discloses several published articles (including Markov et al 1980, Farias et al 1989, Farias et al 1990, Bickler et al 1992, Trimarchi et al 1993 and 1994, and Gobbel et al 1994) which suggest that such presumptions may be wrong, and that if FDP is injected intravenously, it may have substantial neuroactive and anti-ischemic effects inside the brain, in at least some situations.

Without taking a firm position herein on the question of whether FDP can or cannot penetrate the BBB in significant quantities, the Inventors of this application assert that:
(i) several articles published by reputable researchers in high-quality refereed journals contain data which apparently indicate that FDP can penetrate the BBB in significant quantities, in at least some situations;
(ii) if FDP can penetrate the BBB in significant quantities, then it may be able to provide potentially important benefits in at least some patients suffering from stroke or other neurological crises; and,
(iii) pre-diagnostic intravenous injection of FDP will not inflict any known harm on stroke victims, and it may be able to provide a great deal of benefit for patients who are suffering from internal hemorrhaging, or from other types of medical crises that cannot be distinguished from stroke by any person who is likely to be at the site of a medical crisis such as life-threatening injury or unexplained loss of consciousness.

Because of this balance (i.e., little or no risk or downside, balanced against a potentially great benefit), it becomes clear that it is medically advisable to promptly inject FDP (if available, in a convenient injection kit) into someone who has lost consciousness or is suffering from symptoms that indicate the possibility of a stroke, internal hemorrhage, heart attack, or other internal crisis that may involve ischemia or hypoxia.

In summary, FDP may be able to do a great deal of good in many patients suffering from the observable symptoms listed above, while posing no known risk of danger. Accordingly, prompt on-site pre-diagnostic use is warranted in patients who display the symptoms listed above, if such symptoms indicate that the patient is suffering from a medical crisis that is severe enough to warrant a trip to a hospital.

Formulations and Dosages

Any suitable (i.e., pharmacologically acceptable) salt of FDP can be used, such as a sodium salt, or divalent salts such as calcium or magnesium salts, or mixtures thereof. In general, potassium salts should not be administered intravenously, since an abrupt infusion might interfere with cardiac functioning and certain other cellular functions.

However, isomers other than fructose-1,6-diphosphate cannot be used. Although certain other isomers (including fructose-2,6-diphosphate) occur naturally in cells, they serve other purposes and are not created or consumed as intermediates in the glycolysis pathway, and they have no utility for the purposes disclosed herein.

Injectable FDP formulations which are stable for several months when refrigerated can be prepared, packaged, stored, and handled by known and conventional techniques. For example, powdered sterilized FDP can be created by lyophilization and stored in vials, for reconstitution when needed by adding water or a suitable physiological saline solution. Such powdered forms typically will not require refrigeration, although they should be protected against temperatures that can cause degradation.

Alternately, an injectable FDP liquid can be packaged, shipped, and stored in fully hydrated form. Although it preferably should be kept refrigerated as a general measure to increase safety and retard chemical degradation, it will not support active bacterial growth even if not refrigerated, so long as the mixture does not contain any source of nitrogen.

In addition, although there is a general presumption against mixing together different injectable compounds unless they have been thoroughly tested in combination, it is believed that FDP can probably be mixed with one or more other sugar compounds (such as injectable dextrose or glucose, or Ringer's lactate) if desired, without generating any particular adverse effects.

Since FDP should be administered as rapidly as possible in the emergency situations described herein, injection can be carried out using a standard hypodermic syringe, using an initial bolus dosage in the range of about 50 to about 400 mg/kg (i.e., milligrams of FDP per kilogram of patient body weight). Since most adults weigh between 50 and 100 kg (110 to 220 lb), a sterile hypodermic syringe pre-loaded with (for example) 15 g of FDP and carried around in an ambulance or police car, or stored at a nursing home or swimming pool, can provide dosages in the desired range (300 mg/kg for an adult weighing 50 kg, and 150 mg/kg for an adult weighing 100 kg).

In an ambulance, nursing home, or other suitable setting where continuous intravenous infusion can be commenced, an FDP formulation can be infused intravenously either as a 10% solution, or after dilution into sterile infusion bags containing 5% dextrose solution, 0.9% saline, Ringer's lactate, or other conventional intravenous fluids (this generally should exclude formulations used for parenteral feeding or blood transfusions, unless approved by a qualified physician). Such infusions preferably should be within a dosage rate of about 1 to about 5 mg/kg per minute, and may follow an initial bolus injection to make more FDP available to ischemic or hypoxic tissue as rapidly as possible.

EXAMPLES

Example 1

Lyophilization of FDP Solutions

After realizing that FDP's potential as a useful drug has been ignored and neglected by pharmaceutical manufacturers, the Applicant/assignee company, Cypros Pharmaceutical Corporation, commenced a program of developing a suitable lyophilization procedure, to generate a stable and sterile preparation that can be stored for weeks or months and then mixed with water and injected into humans.

This preparation began with a non-sterile bulk powder, manufactured by Boehringer-Mannheim, in Germany. This powder is purchased as a tri-sodium salt. The crystalline form is an octahydrate, with eight molecules of water associated with each molecule of FDP. Calculated water comprises 26.18%, by weight, of this octahydrate salt. Although the concept of "water of hydration" (i.e., the water that remains bound to the FDP when it is in crystalline form) becomes irrelevant after FDP is dissolved in water, a reduction of the water content below 26%, in a lyophilized preparation, requires removal of at least a portion of the water that would remain bound if the FDP were in a normal crystallized form.

During the freezing process, if the FDP forms a glass (i.e., a solid that does not have a regular molecular lattice structure), there will be "sorbed" or "bound" water associated with the non-crystalline material. Such water can be removed by lyophilization. If the product (or some portion thereof) crystallizes during freezing, the product may be an octahydrate or some other hydrated crystalline form, and it is very difficult to remove such water by conventional lyophilization techniques, without melting or altering the crystals.

The bulk powder described above was thoroughly dissolved in water, at varying concentrations starting at about 10% by weight, and ranging up to about 40% by weight. The liquid was pumped through a Gelman "Acrodisc 50" filter with a pore size of 0.2 microns. This sub-micron filtering serves as a sterilization step which removes any bacteria or viral particles. No excipients were added, and the pH was not adjusted.

Filtered sterile solutions were filled into 100 mL molded glass vials. Varying amounts of liquid were loaded into each vial, depending on the concentration of the liquid, to create final quantities of 5 grams of FDP (octahydrate salt) in each vial throughout the tests described herein.

Permeable lyophilization stoppers were placed on the vials, and the vials were loaded onto the shelves in a lyophilization chamber (manufactured by The Virtis Company, Inc., Gardiner, N.Y.) at 13° C. Temperature probes were placed in four interior vials on each shelf.

During the testing phase, all lyophilizations used the same lyophilization chamber, the same supplies (vials, lyophilization stoppers, aluminum stoppers, inert atmospheres, etc.), and the same analytical methods (temperature probes in internal vials, analytical tests, etc.). In various mixtures, the temperature and vacuum conditions were varied, to evaluate optimal combinations and durations.

Initial tests used liquids containing 10% FDP, measured as the weight of the octahydrate salt. Subsequent tests involving 30% to 40% solutions of FDP were subsequently used, since they provided shallower liquid depths, which required shorter processing times.

Typical and suitable temperature and vacuum conditions for lyophilizing a 30% solution of FDP containing tertiary butyl alcohol (TBA) as a secondary vaporizing agent are shown in FIG. 1, as a function of time. Additional data and details are contained in a separate co-pending U.S. patent application, Ser. No. 08/705,773, owned by the same Applicant/assignee company herein. That patent application has been allowed, and it will issue in 1998 as a U.S. patent. The contents of that application (and the patent arising from it) are incorporated herein by reference.

After a drying cycle was completed, the vacuum was released, and nitrogen or argon was bled into the lyophilization chamber. The vials were sealed inside the lyophilizer under an atmosphere of inert gas, at atmospheric pressure. Aluminum overseals were placed on the vials and crimped into place. This generated a dried cake mass which contained water in the range of about 12% to about 16%, by weight. If TBA was used in the solution, the cakes tended to be relatively fragile and easily broken apart to form powders. Subsequent analysis using high performance liquid chromatography indicated that total impurity levels were consistently less than 1% in the FDP preparations made as described above. Shelf life analyses indicate that these preparation can remain stable, without refrigeration, for at least several months.

Example 2

Ability of FDP to Boost Intercellular ATP Levels

In order to be effective in boosting glycolysis and generating ATP, exogenous FDP must be able to permeate or be transported into cell interiors, because that is where glycolysis occurs. Since FDP, with its two phosphate groups, carries a strong negative charge, it is widely presumed to suffer from low permeation rates into cells. A large part of the general skepticism among doctors about the cytoprotective capabilities of FDP apparently centers on this presumed limitation.

To evaluate this factor, human astrocytoma cells which had been grown to confluence were incubated for 1 hour with 1 micromolar of tritium-labelled ($^3$H) adenosine (purchased from Morovek Biochemicals, Inc., Brea, Calif.). Any radiolabelled adenosine which remained in the extra-cellular culture medium was washed out after 1 hour.

The cells were then divided into 2 aliquots. One aliquot was incubated for 6 hours with 3.5 mM FDP, while the other aliquot (containing the control population of cells) was incubated identically, but with no FDP. This allowed cells from a single, identically-treated, same-day population to be used as control cells. This approach was used because when a population of cells is supplied with radio-labelled adenosine, it will generate substantially different radiolabelled ATP readings on different days, depending on various factors such as (1) the status and activity levels of the cells on a specific day, (2) variances between labelling intensity in different batches of radiolabelled reagents, and (3) variances in calibration and settings of the analytical equipment. Because of these differences, count-per-minute data tend to be highly variable between different days, while percentage increases are much more consistent and reliable if a single batch of cells is divided into control and treatment aliquots and then treated and tested on a single day using the same reagents and equipment for both aliquots.

After a 6-hour incubation with or without FDP, both aliquots of cells were killed and extracted with 0.4 M perchloric acid and neutralized with an alanine-freon mixture. ATP concentrations were analyzed using polyethylene imine-cellulose thin layer chromatography. Radioactivity was analyzed in a Beckman liquid scintillation counter.

The results, in Table 1, showed that under normoxic conditions, the addition of FDP to the extra-cellular liquid roughly doubled the quantity of radiolabelled adenosine converted into ATP; treated cell values averaged 198.7 percent of untreated cell values, with a standard deviation of 17%. Under anaerobic conditions, the boosting effect of extra-cellular FDP on intracellular ATP was even stronger; treated cell values were 243±30%. Since the conversion of adenosine to ATP only occurs inside cells, this provides direct evidence that FDP enters mammalian cells in sufficient quantities to substantially increase ATP levels inside the cells.

Example 3

Ability of Intravenous FDP to Decrease Lactic Acid Levels in Blood from Sickly Cell Patients Whole blood samples were taken from patients who suffer from sickle cell disease, but who were not suffering an ischemic crisis at the time; their hematocrit values averaged 24%±6%. Paired samples (4 mL) from each patient were treated with either FDP (5% aqueous solution, 2.5 mg/mL), or with an equivalent amount of glucose. The paired samples were incubated at 37° C. for 25 minutes, and were then homogenized, and deproteinized with 6% perchloric acid. The samples were centrifuged at 4° C., and the supernatant was assayed for ATP, di-hydroxy acetone phosphate (DHAP), pyruvate, and lactic acid.

As a control, whole blood samples were also taken from normal volunteers without any sickling HbS genes (hematocrit=41±4%); such samples were taken both before, and 30 minutes after, an intravenous infusion of FDP in aqueous solution, at dosages of 75 mg/kg (i.e., 75 milligrams of FDP per kilogram of patient body weight). The cells were processed as described above, and the supernatants were tested for ATP levels.

The results are provided in Table 1. In this table, ATP and DHAP values are in micromoles per milliliter; pyruvate values are in milligrams per 100 milliliters; and lactate values are in milligram percent.

TABLE 1

EFFECT OF FDP ON ATP AND LACTATE LEVELS IN HOMOGENIZED WHOLE BLOOD SAMPLES

|  | ATP | DHAP | Pyruvate | Lactate |
| --- | --- | --- | --- | --- |
| Sickle cells, glucose-treated | 1.04 ± 0.01 | 0.14 ± 0.03 | 0.59 ± 0.09 | 46.6 ± 2.59 |
| Sickle cells, FDP-treated | 2.17 ± 0.13 | 1.23 ± 0.05 | 1.52 ± 0.01 | 36.2 ± 2.16 |
| Normal cells, before FDP infusion | 2.88 ± 0.13 | 0.05 ± 0.04 | 1.20 ± 0.07 | 7.66 ± 0.16 |
| Normal cells, after i.v. FDP infusion | 3.29 ± 0.16 | 0.08 ± 0.05 | 1.08 ± 0.08 | 6.34 ± 0.55 |

These results indicate that treatment with FDP more than doubled the ATP concentrations, in whole blood samples from patients with sickle cell anemia (who were not suffering a crisis at the time). FDP also slightly increased ATP levels, in whole blood samples from volunteers who do not have sickle cell anemia.

Surprisingly, and more importantly for the current invention, FDP also lowered the levels of lactic acid, in whole blood samples from both (i) treated sickle cell patients, and (ii) volunteers who do not have the disease.

An additional set of in vitro tests were carried out on blood samples taken from four sickle cell patients. The patients were not suffering from sickling crises at the time the blood was sampled; however, the blood samples were subjected to hypoxia, by bubbling nitrogen gas through the samples until sickling occurred.

These tests compared saline-treated and glucose-treated controls against FDP treatments using two different concentrations (5 or 10 mg/mL of FDP). The results are as follows:

TABLE 2

EFFECT OF FDP ON RED CELL METABOLITES

| Metabolite | Saline Control | Glucose Control | FDP 5 mg/mL | FDP 10 mg/mL |
| --- | --- | --- | --- | --- |
| ATP, μmol/mL | 0.8 ± 0.08 | 0.99 ± 0.12 | 1.76 ± 0.03 | 2.86 ± 0.1 |
| DHAP, μmol/mL | 0.31 ± 0.01 | 0.17 ± 0.02 | 3.30 ± 0.12 | 3.90 ± 0.29 |
| Pyruvate, mg/dL | 11.6 ± 1.8 | 10.8 ± 0.75 | 11.8 ± 0.9 | 11.1 ± 1.08 |
| Lactate, mg/dL | 91.5 ± 5.8 | 214.8 ± 11 | 110 ± 8.7 | 105 ± 14 |

In these tests, FDP caused an increase in ATP and DHAP levels, in a dose-dependent manner. The effects on lactate deserve attention, and several trends should be noted, including:

(i) The slight increases in lactate at both dosages of FDP did not rise to a level of statistical significance, compared to the saline controls;

(ii) the higher dosage of FDP did not cause any increase in lactate levels, compared to the lower dosage of FDP;

(iii) the slight increases in lactate levels from FDP (compared to controls) was very minor, compared to the very large increase in lactate levels caused by glucose treatment.

Example 4

Safety of FDP in Compromised Patients Undergoing Cardiac Surgery

Tests were carried out to evaluate the benefits of FDP in reducing ischemic heart damage in patients who were undergoing circulatory bypass of the heart during coronary artery bypass grafting (CABG) surgery. In these tests, coronary bypass patients were pre-treated with an intravenous infusion of FDP at a dosage of 250 mg of FDP per kilogram of patient body weight, beginning about 10 to 30 minutes before circulatory bypass began. This gave the FDP sufficient time to permeate into the heart tissue before it was subjected to ischemic conditions under cardioplegia.

As indicated in FIGS. 3–6, pre-bypass injection of FDP significantly reduced the level of ischemic damage that was inflicted on treated patients, compared to control populations that did not receive any FDP, as measured by both biochemical and mechanical means. On a biochemical level, as shown in FIG. 4, FDP significantly reduced the amount of an enzyme called creatine kinase (CK) which was released into blood by cells. Since CK is a very large intracellular protein that cannot be transported across intact cell membranes, this enzyme is commonly used as an indicator of the extent of heart cell death and permanent tissue damage in cardiac patients.

On a mechanical level, pre-bypass treatment with FDP also substantially reduced a hemodynamic abnormality which involves an increase in "pulmonary artery wedge pressure" (PAWP), as shown in FIG. 5. An increase in PAWP values indicates that a patient's heart has suffered some sort of damage or is struggling with some form of abnormal stress. Nearly all cardiac surgery patients undergo an increase in PAWP values in the hours or days after surgery.

If a drug can reduce the undesired increases in PAWP values, it indicates that the drug apparently helped reduce the severity of the stress that was imposed on the heart by the surgery.

As shown in FIG. 6, there was a correlation between the biochemical and hemodynamic/mechanical benefits of pre-bypass treatment using FDP. The ability of FDP to reduce the indicators of stress and damage in the heart, using two independent measurements, confirm that FDP can truly benefit the heart and reduce heart stress and damage during circulatory bypass when the heart muscle must undergo a period of ischemia.

Blood acidity (which indicates lactic acid accumulation) also was monitored in all patients in this trial. The only patients who showed a slight but significant decrease in blood pH (lower pH indicates higher acidity, which indicates that levels of lactic acid in the blood have increased) were patients in one group that received very high dosages of FDP (250 mg/kg pre-operative, plus another 250 mg/kg at 2 hours after bypass was terminated, plus another 250 mg/kg at 6 hours after bypass was terminated, for a total of 750 mg/kg over a span of about 7 or 8 hours total). The reductions in blood pH were deemed minor, and were not significant enough to merit treatment with sodium bicarbonate to reverse the trend. None of the patients who received lower quantities of FDP showed any significant alterations in blood pH, which indicates that any lactic acid which was formed from injected FDP was easily handled by the patient's normal metabolic functions.

These tests were carried out on 20 patients, under the supervision of a qualified cardiac anesthesiologist. These tests were initiated and sponsored by cypros Pharmaceutical Corporation (the assignee and applicant herein), which obtained approval from the United States Food and Drug Administration prior to carrying out these Phase II human clinical trials. Phase I trial requirements (to establish baseline values for FDP using tests on healthy volunteers) were waived by the F.D.A., since FDP is a naturally occurring biochemical that occurs only as a short-lived intermediate which is quickly consumed during glycolysis.

These tests were carried out using placebo-controlled, double-blind randomized design, and were performed in accordance with all FDA guidelines for good clinical practice (GCP). To the best of the Applicant's knowledge, this was the first such clinical trial ever conducted which tested FDP as a protective agent in this manner or for this use, and there is no other comparable agent being used for this purpose anywhere in the world.

All of the patients who were tested were medically compromised and in poor health. A number had already suffered heart attacks, and all were suffering from coronary artery occlusions that were severe enough to require open-chest surgery, rather than balloon angioplasty, drug treatment, or other less-invasive procedures.

During these tests, there was no indication whatsoever of any adverse effects of FDP on any of the patients. Furthermore, since FDP is a short-lived intermediate which is quickly consumed by glycolysis, there is every reason to believe that FDP poses no significant risks, or only very low and minimal risks of any significant adverse effects, in patients who may not need it. It should also be noted that the requirement for Phase I tests (which are sometimes needed to establish baseline values on healthy people, who serve as "control" populations) was considered unnecessary, and was waived, by the U.S. Food and Drug Administration, when Cypros Pharmaceutical Corporation applied to the FDA to carry out the clinical tests described herein. To the best of the Applicant's knowledge and belief, these are the first clinical data ever reported on FDP which were gathered in tests that were carried out under the full auspices of FDA-approved "Good Clinical Practices".

Thus, there has been shown and described a new and useful method for on-site medical treatment of patients who are suffering from life-threatening medical emergencies. This treatment can be carried out by anyone trained to administer an intravenous injection, without waiting for access to a fully trained physician and diagnostic equipment. Although this method of treatment has been exemplified for purposes of illustration and description by reference to certain specific embodiments, it will be apparent to those skilled in the art that various modifications, alterations, and equivalents of the illustrated examples are possible. Any such changes which derive directly from the teachings herein, and which do not depart from the spirit and scope of the invention, are deemed to be covered by this invention.

References

Angelos, M. G., et al, "FDP fails to limit early myocardial infarction size in a canine model," Ann. Emerg. Med. 22: 171–177 (1993)

Bickler, P. E., et al, "FDP stabilizes brain intracellular calcium during hypoxia in rats," Stroke 23: 1617–22 (1992)

Brunswick, R., et al, "Preservation of myocardium by infusion of FDP following coronary occlusion," Am J Cardiol 49: 1008 (1982)

Cacioli, D., et al, "Haemorheological effects of FDP in patients with lower extremity ischaemia," Curr Med Res Opin 10: 668–74 (1988)

Eddy, L. J., et al, "Lack of a direct metabolic effect of FDP in ischemic myocardium," Am J Physiol 241: H576–83 (1995)

Farias, L. A., et al, "Prevention of ischemic-hypoxic brain injury and death in rabbits with FDP," Stroke 21: 606–13 (1990)

Farias, L. A., et al, "Effects of FDP, glucose and saline on cardiac resuscitation," Anesthesiology 65: 595–601 (1986)

Farias, L. A., et al, "Improved brain metabolism with FDP during insulin-induced hypoglycemic coma," Am J Med Sci 297: 294–9 (1989)

Gobbel, G. T., et al, "Response of cerebral endothelial cells to hypoxia: modification by FDP but not glutamate receptor antagonists," Brain Res 653: 23–30 (1994)

Grandi, A. M., et al, "Improved left ventricular function after short-term treatment with FDP," Clin Ther 10: 372–80 (1988)

Granot, H., et al, "Successful treatment of irreversible hemorrhagic shock in dogs with FDP and dichloroacetate," Circ Shock 163–73 (1985)

Lazzarino, G., et al, "Ischemia and reperfusion: effect of FDP," Free Radic Res Commun 16: 325–39 (1992)

Lazzarino G., et al, "Protective effects of exogenously administered FDP from ischemia reperfusion damage induced on isolated rat heart," Ital J Biochem 38: 251A–253A (1989)

Markov, A. K., et al, "Hemodynamic, electrocardiographic, and metabolic effects of FDP on acute myocardial ischemia," Am Heart J 100: 639–46 (1980)

Markov, A. K., "Hemodynamics and metabolic effects of FDP in ischemia and shock—experimental and clinical observations," Ann Emerg Med 15: 1470–7 (1986)

Markov, A. K., et al, "Increasing survival of dogs subjected to hemorrhagic shock by administration of FDP," *Surgery* 102: 515–27 (1987)

Pasque, M. K., et a, "Metabolic intervention to affect myocardial recovery following ischemia," *Annals of Surgery* 200: 1–12 (1984)

Sano, W., et al, "Beneficial effect of FDP on mitochondrial function during ischemia-reperfusion of rat liver," *Gastroenterology* 108: 1785–92 (1995)

Tortosa, A., et al, "FDP fails to ameliorate delayed neuronal death in the CA1 area after transient forebrain ischaemia in gerbils," *Neuropharmacology* 32: 1367–71 (1992)

Trimarchi, G. R., et al, "Neuroprotective activity of FDP following transient forebrain ischemia in the Mongolian gerbil," *Japan J Pharmacol* 62: 215–22 (1993)

Trimarchi, G. R., et al, "Effects of FDP on brain polyamine biosynthesis in a model of transient cerebral ischemia," *Life Sci* 54: 1195–204 (1994)

Zhang, J. N., et al, "Protective effect of exogenous FDP in cardiogenic shock," *Cardiovasc Res* 22: 927–32 (1988)

We claim:

1. A method for emergency treatment of a patient who is suffering from a life-threatening medical crisis, comprising the step of intravenously injecting into the patient, as quickly as possible and without waiting to obtain a medical diagnosis of the patient by a physician, fructose-1,6-diphosphate or a salt thereof, in a dosage which is therapeutically effective in reducing ischemic damage to at least one internal organ in a patient at risk of such damage.

2. The method of claim 1, wherein the fructose-1,6-diphosphate or salt thereof is obtained from a sealed vial which contains fructose-1,6-diphosphate or a salt thereof in a sterile lyophilized form which is chemically stable without requiring refrigeration and which can be mixed with a sterile aqueous solution to create an injectable formulation.

3. The method of claim 2, wherein the sealed vial which contains fructose-1,6-diphosphate or a salt thereof is a component of an injection kit which also contains:
    (a) a sterile aqueous solution, in a quantity which is suited for mixing with the fructose-1,6-diphosphate or a salt thereof to form an injectable formulation;
    (b) at least one hypodermic needle;
    (c) a syringe suited for holding the injectable formulation and for injecting the injectable formulation intravenously into the patient; and,
    (d) means for transferring the injectable formulation into the syringe without exposing the injectable formulation to outside air and an attendant risk of contamination.

4. The method of claim 1, wherein fructose-1,6-diphosphate is injected into the patient in an initial bolus having a dosage within a range of about 50 to about 400 milligrams of fructose-1,6-diphosphate per kilogram of patient body weight.

5. The method of claim 1, wherein an initial body injection of fructose-1,6-diphosphate is followed by intravenous infusion of fructose-1,6-diphosphate at a dosage within a range of about 1 to about 5 milligrams of fructose-1,6-diphosphate per kilogram of patient body weight, per minute.

6. A method for emergency treatment of a patient who is suffering from an undiagnosed but potentially life-threatening medical crisis, comprising the step of intravenously injecting into the patient fructose-1,6-diphosphate or a salt thereof, in a dosage which is therapeutically effective in reducing ischemic damage to at least one internal organ, wherein the intravenous injection is administered prior to diagnosis of the medical crisis by a physician.

7. The method of claim 6, wherein the intravenous injection is administered to a patient at the site of an event selected from the group consisting of:
    a. a traumatic injury involving loss of blood;
    b. a near-asphyxiation of the patient;
    c. an unexplained loss of consciousness by the patient;
    d. an unexplained episode of mental incoherence or disorientation in the patient;
    e. an unexplained loss of the ability to control motor functions by the patient;
    f. severe yet unexplained shortness of breath.

8. The method of claim 6, wherein the fructose-1,6-diphosphate or salt thereof is obtained from a sealed vial which contains fructose-1,6-diphosphate or a salt thereof in a sterile lyophilized form which is chemically stable without requiring refrigeration and which can be mixed with a sterile aqueous solution to create an injectable formulation.

9. The method of claim 8, wherein the sealed vial which contains fructose-1,6-diphosphate or a salt thereof is a component of an injection kit which also contains:
    (a) a sterile aqueous solution, in a quantity which is suited for mixing with the fructose-1,6-diphosphate or a salt thereof to form an injectable formulation;
    (b) at least one hypodermic needle;
    (c) a syringe suited for holding the injectable formulation and for injecting the injectable formulation intravenously into the patient; and,
    (d) means for transferring the injectable formulation into the syringe without exposing the injectable formulation to outside air and an attendant risk of contamination.

10. The method of claim 8, wherein an initial bolus injection of fructose-1,6-diphosphate is followed by intravenous infusion of fructose-1,6-diphosphate at a dosage within a range of about 1 to about 5 milligrams of fructose-1,6-diphosphate per kilogram of patient body weight, per minute.

11. The method of claim 6, wherein fructose-1,6-diphosphate is injected into the patient in an initial bolus having a dosage within a range of about 50 to about 400 milligrams of fructose-1,6-diphosphate per kilogram of patient body weight.

12. An injection kit containing all components necessary to rapidly inject a sterile injectable formulation of fructose-1,6-diphosphate or a salt thereof into a patient who is suffering from a life-threatening medical crisis, comprising:
    (a) at least one sealed vial which contains fructose-1,6-diphosphate or a salt thereof, in a sterile lyophilized form which is chemically stable without requiring refrigeration and which can be mixed with a sterile aqueous solution to create an injectable formulation, in a dosage which is therapeutically effective in reducing ischemic damage to at least one internal organ in a patient at risk of such damage;
    (b) a sterile aqueous solution, in a quantity suited for mixing with the fructose-1,6-diphosphate or a salt thereof to form an injectable formulation;
    (c) means for mixing the fructose-1,6-diphosphate or salt thereof with the sterile aqueous solution in a manner which does not expose either component to outside air;

(d) at least one hypodermic needle;

(e) a syringe suited for holding the injectable formulation and for injecting the injectable formulation intravenously into a patient; and, (f) means for transferring the injectable formulation into the syringe without exposing the injectable formulation to outside air.

13. An injection kit of claim 12, wherein the sterile lyophilized form of fructose-1,6-diphosphate or a salt thereof contains a residual water content in a range of at least 10% up to about 25%, by weight.

14. An injection kit of claim 12, wherein the sterile lyophilized form of fructose-1,6-diphosphate or a salt thereof contains a residual water content in a range of about 12% to about 16%, by weight.

15. An injection kit of claim 12, wherein the sterile lyophilized form of fructose-1,6-diphosphate or a salt thereof contains no more than about 1% total impurities, by weight.

* * * * *